United States Patent

Arimura et al.

[11] 3,932,423
[45] Jan. 13, 1976

[54] IMIDAZOLIDO(1,5-C)THIAZOLIDINE-3-SPIRO-4-PIPERIDINES

[75] Inventors: Katsuo Arimura; Hideki Ao, both of Nakatsu, Japan

[73] Assignee: Yoshitomi Pharmaceutical Industries, Osaka, Japan

[22] Filed: May 28, 1974

[21] Appl. No.: 473,977

[30] Foreign Application Priority Data
May 28, 1973 Japan.............................. 48-59991
July 4, 1973 Japan.............................. 48-76009
Aug. 14, 1973 Japan.............................. 48-91595
Aug. 14, 1973 Japan.............................. 48-91596

[52] U.S. Cl.......... 260/293.57; 260/240 K; 424/267
[51] Int. Cl.²..................................... C07D 513/20
[58] Field of Search.............................. 260/293.57

[56] References Cited
UNITED STATES PATENTS
3,632,816   1/1972   Paolini et al..................... 260/306.7

Primary Examiner—G. Thomas Todd
Attorney, Agent, or Firm—Sughrue, Rothwell, Mion & Zinn

[57] ABSTRACT

Imidazolido[1,5-c]thiazolidine-3-spiro-4'-piperidine compounds of the formula:

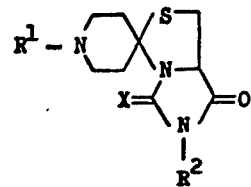

wherein $R^1$ represents a member selected from the group consisting of a hydrogen atom, an alkyl group of from 1 to 4 carbon atoms, a benzyl group, a p-chlorobenzyl group, a 4,5-dimethoxybenzyl group, a 4,5,6-trimethoxybenzyl group, a phenethyl group, an acetyl group, a benzoyl group, a trimethoxybenzoyl group, a methoxycarbonyl group, an ethoxycarbonyl group, a 4,4-bis(p-fluorophenyl)butyl group and a group of the formula

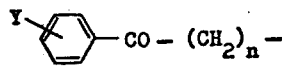

(in which Y represents a member selected from the group consisting of H, F and $CH_3O$, and n represents an integer of 1, 2 or 3); $R^2$ represents a member selected from the group consisting of a hydrogen atom, an alkyl group of from 1 to 4 carbon atoms, an allyl group, a propargyl group, a cyclohexyl group, a phenyl group, a chlorophenyl group, a dichlorophenyl group, a tolyl group, a nitrophenyl group, a naphthyl group, a benzyl group, a phenethyl group and a cinnamyl group; and X represents a member selected from the group consisting of an oxygen atom and a sulphur atom; and pharmaceutically acceptable acid addition salts thereof. These compounds are useful as drugs for the treatment of schizophrenia, mania and various psychoneuroses.

10 Claims, No Drawings

IMIDAZOLIDO(1,5-C)THIAZOLIDINE-3-SPIRO-4-PIPERIDINES

This invention relates to novel and therapeutically valuable compounds of the formula:

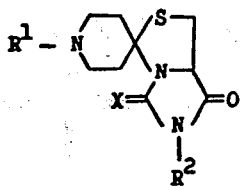

(I)

and pharmaceutically acceptable acid addition salts thereof.

In the above formula, $R^1$ represents a member selected from the group consisting of a hydrogen atom, an alkyl group of from 1 to 4 carbon atoms, a benzyl group, a p-chlorobenzyl group, a 4,5-dimethoxybenzyl group, a 4,5,6-trimethoxybenzyl group, a phenethyl group, an acetyl group, a benzoyl group, a trimethoxybenzoyl group, a methoxycarbonyl group, an ethoxycarbonyl group, a 4,4-bis(p-fluorophenyl)butyl group and a group of the formula

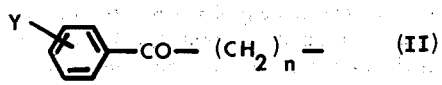

(II)

(in which Y represents a member selected from the group consisting of H, F and $CH_3O$, and $n$ represents an integer of 1, 2 or 3); $R^2$ represents a member selected from the group consisting of a hydrogen atom, an alkyl group of from 1 to 4 carbon atoms, an allyl group, a propargyl group, a cyclohexyl group, a phenyl group, a chlorophenyl group, a dichlorophenyl group, a tolyl group, a nitrophenyl group, a naphthyl group, a benzyl group, a phenethyl group and a cinnamyl (or 3-phenylallyl) group; and X represents a member selected from the group consisting of an oxygen atom and a sulphur atom.

The compounds of formula (I) can be produced by one of the following methods (a) to (d):

a. By reacting a compound of the formula

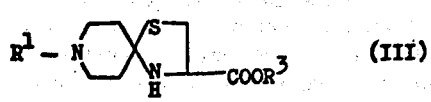

(III)

wherein $R^3$ represents an alkyl group of from 1 to 4 carbon atoms and $R^1$ is as defined above, with a compound of the formula $$R^{2\prime} - NCX \qquad (IV)$$

or a cyanate or thiocyanate, wherein $R^{2\prime}$ represents a member selected from the group consisting of an alkyl group of from 1 to 4 carbon atoms, an allyl group, a propargyl group, a cyclohexyl group, a phenyl group, a chlorophenyl group, a dichlorophenyl group, a tolyl group, a nitrophenyl group, a naphthyl group, a benzyl group, a phenethyl group and a cinnamyl group.

When the compound of formula (IV) is used as one of the reactants, the reaction is usually carried out in a solvent under anhydrous conditions at a temperature of from room temperature to about the boiling point of the solvent employed for a period of from 1 to 30 hours. The said solvent is, for example, an aromatic hydrocarbon (e.g. benzene, toluene, xylene), a halogenated hydrocarbon (e.g. chloroform, dichloroethane, chlorobenzene), an ether (e.g. diethyl ether, tetrahydrofuran, dioxane), an ester (e.g. ethyl acetate, butyl acetate) or a tertiary amine (e.g. triethylamine, N,N-diethylaniline, pyridine). When the reaction is carried out in a solvent other than the tertiary amine, it is advantageous to add a small amount of the tertiary amine.

When such (thio)cyanate as KOCN, NaOCN, $NH_4OCN$, KSCN or $NH_4SCN$ is used, the reaction is carried out in glacial acetic acid or a mixture of glacial acetic acid and water at a temperature of from room temperature to an elevated temperature (e.g. 60°–75°C) for a period of about 3 hours, and the compounds of formula (I) wherein $R^2$ represents a hydrogen atom are produced.

b. In order to produce the compounds of formula (I) wherein $R^1$ represents a member selected from the group consisting of an alkyl group of from 1 to 4 carbon atoms, a benzyl group, a p-chlorobenzyl group, a 4,5-dimethoxybenzyl group, a 4,5,6-trimethoxybenzyl group, a phenethyl group, an acetyl group, a benzoyl group, a trimethoxybenzoyl group, a methoxycarbonyl group, an ethoxycarbonyl group, a 4,4-bis(p-fluorophenyl)-butyl group and a group of formula (II); by reacting a compound of the formula $$R^{1\prime} - Z \qquad (V)$$

wherein Z represents a member selected from the group consisting of a halogen atom (e.g. Cl, Br, I), an alkylsulfonyloxy group (e.g. methylsulfonyloxy) and an arylsulfonyloxy group (e.g. phenylsulfonyloxy, p-tolylsulfonyloxy), and $R^{1\prime}$ represents a member selected from the group consisting of an alkyl group of from 1 to 4 carbon atoms, a benzyl group, a p-chlorobenzyl group, a 4,5-dimethoxybenzyl group, a 4,5,6-trimethoxybenzyl group, a phenethyl group, an acetyl group, a benzoyl group, a trimethoxybenzoyl group, a methoxycarbonyl group, an ethoxycarbonyl group, a 4,4-bis(p-fluorophenyl)butyl group, a group of formula (II) and a group of the formula

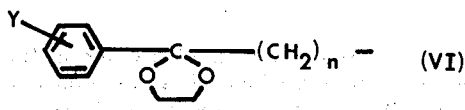

(VI)

(in which Y and $n$ are as defined above), with a compound of the formula

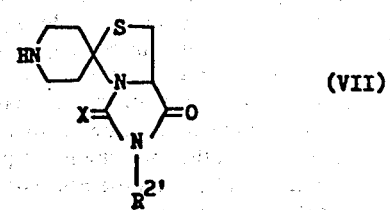

(VII)

wherein each symbol is as defined above, and then, in the case of the compound of formula (V) wherein $R^{1\prime}$ represents a group of formula (VI), by hydrolyzing the compound thus obtained of the formula

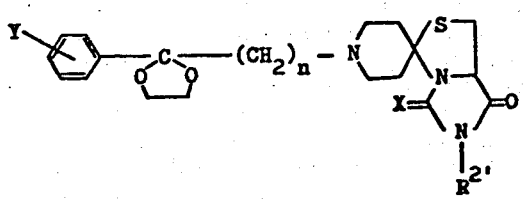

(VIII)

wherein each symbol is as defined above.

The reaction of compound (V) with compound (VII) is carried out in a solvent in the presence of a deacidifying agent at a temperature around the boiling point of the solvent employed for a period of from 2 to 30 hours. The said solvent is, for example, an alcohol (e.g. methanol, ethanol, 2-propanol), a ketone (e.g. acetone, methyl ethyl ketone), an aromatic hydrocarbon (e.g. benzene, toluene, xylene), an ether (e.g. dioxane, tetrahydrofuran), an ester (e.g. ethyl acetate, butyl acetate) or an amide (e.g. dimethylformamide, diethylformamide, dimethylacetamide). The said acidifying agent is an alkali metal carbonate (e.g. $Na_2CO_3$, $K_2CO_3$), an alkali metal bicarbonate (e.g. $NaHCO_3$, $KHCO_3$), an alkali metal hydroxide (e.g. NaOH, KOH), an alkali metal alkoxide (e.g. sodium ethoxide, potassium methoxide) or a tertiary amine (e.g. triethylamine, N,N-dimethylaniline, N,N-diethylaniline, pyridine).

The hydrolysis is carried out by treating the compound of formula (VIII) with a dilute acid (e.g. dilute hydrochloric, dilute sulfuric acid) at room temperature or an elevated temperature.

c. In order to produce the compounds of formula (I) wherein $R^1$ represents a hydrogen atom, by eliminating the alkoxycarbonyl group in a compound of the formula

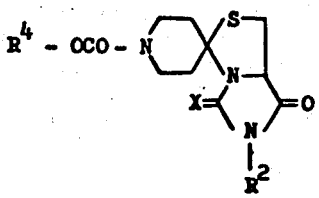

(IX)

wherein $R^4$ represents an alkyl group of from 1 to 2 carbon atoms and $R^2$ and X are as defined above.

The alkoxycarbonyl elimination is carried out by treating a compound of formula (IX) with an acid such as hydrogen chloride, hydrogen bromide, hydrogen fluoride or perchloric acid in a solvent, preferably with 10–25 percent hydrogen bromide in acetic acid, at a temperature of about the boiling point of the solvent employed for a period of from 0.5 to 3 hours, or with an alkali such as sodium hydroxide, potassium hydroxide, barium hydroxide or calcium hydroxide in a solvent such as water, methanol, ethanol, 2-propanol, butanol or ethylene glycol at a temperature of about the boiling point of the solvent employed for a period of from 1 to 12 hours.

d. In order to produce the compounds of formula (I) wherein $R^2$ represents a member selected from the group consisting of an alkyl of from 1 to 4 carbon atoms, an allyl group, a propargyl group, a cyclohexyl group, a phenyl group, a chlorophenyl group, a tolyl group, a nitrophenyl group, a naphthyl group, a benzyl group, a phenethyl group and a cinnamyl group, by reacting a compound of the formula

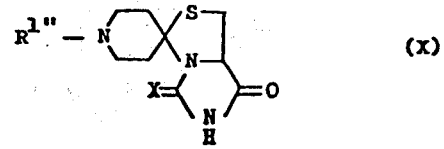

(X)

wherein $R^{1'''}$ represents a member selected from the group consisting of an alkyl group of from 1 to 4 carbon atoms, a benzyl group, a p-chlorobenzyl group, a 4,5-dimethoxybenzyl group, a 4,5,6-trimethoxybenzyl group, a phenethyl group, an acetyl group, a benzoyl group, a trimethoxybenzoyl group, a methoxycarbonyl group, an ethoxycarbonyl group, a 4,4-bis(p-fluorophenyl)-butyl group and a group of formula (II), and X is as defined above, with a compound of the formula $$R^{2'} - Z \qquad (XI)$$

wherein $R^{2'}$ and Z are as defined above.

The reaction is usually carried out in a solvent such as an alcohol (e.g. methanol, ethanol, 2-propanol, butanol), an amide (e.g. dimethylformamide, diethylformamide, dimethylacetamide), a ketone (e.g. acetone, methyl ethyl ketone), an aromatic hydrocarbon (e.g. benzene, toluene, xylene), an ether (e.g. dioxane, tetrahydrofuran) or an ester (e.g. ethyl acetate, butyl acetate) in the presence of a deacidifying agent such as an alkali metal carbonate (e.g. $Na_2CO_3$, $K_2CO_3$), an alkali metal bicarbonate (e.g. $NaHCO_3$, $KHCO_3$), an alkali metal hydroxide (e.g. NaOH, KOH), an alkali metal alkoxide (e.g. sodium ethoxide, potassium methoxide) or a tertiary amine (e.g. triethylamine, N,N-dimethylaniline, N,N-diethylaniline, pyridine) at a temperature of from room temperature to about the boiling point of the solvent employed for a period of from 2 to 8 hours. Alternatively this reaction is preferably carried out by treating a compound of formula (X) with an alkali metal hydroxide (e.g. NaOH, KOH) or an alkali metal hydride (e.g. NaH, KH), and then by reacting the alkali metal salt thus obtained, with or without isolation, with a compound of formula (XI).

The compounds of formula (I) can be converted into acid addition salts with various inorganic acids (e.g. hydrochloric, hydrobromic, sulfuric, nitric acid) or with inorganic acids (e.g. oxalic, maleic, fumaric, tartaric, citric acid).

The starting compounds of formula (III) can be produced by reacting a compound of the formula

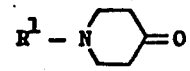

wherein $R^1$ is as defined above, with a compound of the formula

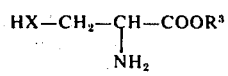

wherein X and R³ are as defined above.

The reaction is carried out in a solvent such as methanol, ethanol, 2-propanol, butanol or dimethylformamide at a temperature about the boiling point of the solvent employed for a period of from 1 to 3 hours.

Specific example of the preparation of the starting compound of formula (III) is as follows:

To a mixture of 19 g. of 1-benzyl-4-oxopiperidine and 100 ml. of ethanol is added a mixture of 15 ml. of concentrated hydrochloric acid and 14 g. of L-cysteine hydrochloride, and the whole mixture is refluxed for 8 hours. The ethanol is distiled off under reduced pressure. The residue is dissolved in water and made alkaline with potassium carbonate. The oil liberated is extracted with chloroform and the extract is washed with water and dried. The chloroform is distiled off and the residue is recrystallized twice from n-hexane to give 23 g. of 8-benzyl-3-ethoxycarbonyl-1-thia, 4,8-diazaspiro[4.5]decane as white crystals melting at 67°–68°C. Its dihydrochloride melts at 193°C with decomposition.

The following starting compounds of formula (III) are also producible by a similar manner, for example:

3-ethoxycarbonyl-8-(4-p-fluorophenyl-4-oxobutyl)-1-thia-4,8-diazaspiro[4.5]decane, M.p. 84°–85°C; its dihydrochloride, M.p. 198°–199°C (decomposition);
3-ethoxycarbonyl-8-methyl-1-thia-4,8-diazaspiro[4.5]-decane dihydrochloride, M.p. 206°–207°C (decomposition);
3,8-diethoxycarbonyl-1-thia-4,8-diazaspiro[4.5]decane hydrochloride, M.p. 171°–172°C; and
8-cinnamyl-3-ethoxycarbonyl-1-thia-4,8-diazaspiro[4.5]decane dihydrochloride, M.p. 198°C (decomposition).

The compounds of formula (I) and pharmaceutically acceptable acid addition salts thereof possess excellent pharmacological properties such as suppression of spontaneous motility, reserpine potentiation, antimescaline effect and suppression of fighting behavior and are useful as drugs for the treatment of schizophrenia, mania and various psychoneuroses.

For example, 5,7-dioxo-6-methylimidazolido[1,5-c]thiazolidine-3-spiro-4'-[1'-(4-p-fluorophenyl-4-oxobutyl)piperidine] (compound A) of the present invention is tested according to the following methods:

METHODS i. Suppression of Spontaneous Motility

Each group consisting of 5 male mice, dd-strain weighing 20 to 25 g., was kept in a compartment (20 × 40 × 20 cm.). The spontaneous motility of mice was counted by magnetic counter of photocell method according to P. B. Dews in "British Gournal of Pharmacology", vol. 8, p. 46 ff. (1953). Forty minutes after the intraperitoneal administration of the test compound, the spontaneous motility was counted for 20 minutes. The $ED_{50}$ shows the dose required for 50 percent suppression of spontaneous motility.

ii. Suppression of Fighting Behavior

Fighting episodes were produced in mice by the method described by Tedeschi et al. in "Journal of Pharmacology and Experimental Therapeutics," vol. 125, p. 28 ff. (1959). Each group consisting of 6 female mice (3 pairs), dd-strain weighing 20 to 25 g., was given orally the test compound 60 minutes prior to receiving electric foot-shock for 3 minutes with an interrupted current of 650 volts, 1.3 milliamperes, 10 cycles per second. In case 3 fighting episodes or less within 3 minutes were exhibited, the pair of mice was deemed to be suppressed by the test compound. The control mice of 81 pairs showed the fighting episodes of 8.7 times on the average under the same conditions. The $ED_{50}$, the dose required to suppress 50 percent of fighting pairs, was determined graphically.

iii. Reserpine Potentiation

Reserpine potentiation was measured by the method described by M. D. Aceto in "Toxicology and Applied Pharmacology," vol. 7, p. 329 ff. (1965). Thirty minutes after the oral administration of the test compound to female mice (dd-strain weighing 20 to 25 g., each group consisting of four animals), reserpine (10 mg./kg. of body weight) was injected intraperitoneally. The degree of blepharoptosis of both eyes was observed 15, 60, 120 and 180 minutes after the administration of reserpine. The $PD_{30}$ shows an effective dose potentiating the effect of reserpine by 30 percent 15 minutes after the administration of reserpine.

iv. Antimescaline Effect

A modification of the method of R. A. Turner [Screening Method in Pharmacology, Edited by R. A. Turner, p. 73, Academic Press (1965)] was used to study the prevention of scratching episodes induced by mescaline. The test compound was given to groups each of 6 female mice orally 60 minutes prior to treatment with mescaline sulfate (30 mg./kg. of body weight, intraperitoneal). Ten minutes later, the effect of test compound on the scratching episodes was observed for 10 minutes. The $ED_{50}$ shows the dose required for prevention of scratching in 50 percent of the animals.

v. Methamphetamine Group Toxicity

Methamphetamine group toxicity was tested according to the method described by G. B. Fink and R. E. Larson in "Journal of Pharmacology and Experimental Therapeutics," vol. 137, p. 361 ff. (1962). Groups each of 10 female mice, dd-strain weighing 20 to 25 g., was placed in a plastic pot (200 cm², 18.7 cm heigh ). The test compound was given orally 2 hours prior to treatment with methamphetamine (9 mg./kg. of body weight, intraperitoneal), and $ED_{50}$ that dose for 50 percent inhibition of mortality was determined graphically from the mortality within 5 hours. The ambient temperature and humidity were kept constant at 25.0° ± 0.5°C, 55 ± 5 percent respectively.

vi. Acute Toxicity

The test compound was orally administered to groups each of 5 female mice respectively. The $LD_{50}$ was calculated from the lethal rate (50 percent) within two days after administration of the test compound.

Results

| Compounds / Actions | Compound A | Floropipamide (for comparison) |
| --- | --- | --- |
| Suppression of Spontaneous Motility, $ED_{50}$ (mg./kg.) (i.p.) | 0.1 | 1.0 |
| Suppression of Fighting Behavior, $ED_{50}$ (mg./kg.) (p.o.) | 2.6 | 5.6 |
| Reserpine Potentiation $PD_{30}$ (mg./kg.) (p.o.) | 1.9 | 2.5 |
| Antimescaline Effect $ED_{50}$ (mg./kg.) (p.o.) | 0.1 | 1.0 |
| Methamphetamine Group Toxicity, $ED_{50}$ (mg./kg.) (p.o.) | 1.1 | 9.2 |
| Acute Toxicity $LD_{50}$ (mg./kg.) (p.o.) | >1000 | >1000 |

In view of the tests including those mentioned above, the compounds (I) of the present invention and pharmaceutically acceptable acid addition salts thereof can be administered safely as psychotropic agents for the treatment of schizophrenia, mania and the like, in the form of a pharmaceutical preparation with a suitable and conventional carrier or adjuvant, administered orally, without harm to the patient.

The oral daily dose of compound (I) or a salt thereof for human adults usually ranges from 5 to 50 milligrams.

The pharmaceutical preparations can take any conventional form such as tablets, capsules, powders, granules, injectable solution, etc.

Formulation Examples i. 5 mg. and 10 mg. tablets are prepared from the following compositions:

|  | 5 mg. Tablet | 10 mg. Tablet |
| --- | --- | --- |
| Compound A | 5.00 mg. | 10.00 mg. |
| Lactose | 35.00 mg. | 30.00 mg. |
| Corn Starch | 20.00 mg. | 20.00 mg. |
| Microcrystaline Cellulose | 5.00 mg. | 5.00 mg. |
| Talc | 4.55 mg. | 4.55 mg. |
| Methyl Cellulose | 0.45 mg. | 0.45 mg. |
|  | 70.00 mg. | 70.00 mg. | ii. Injectable solution containing 10 mg. of compound A per ml. is prepared from the following compositions:

| | |
| --- | --- |
| Compound A | 10.0 mg. |
| Lactic acid | 5.0 mg. |
| Glucose | 30.0 mg. |
| Water for Injection | A sufficient amount to make 1 ml. |

The present invention will be better understood from the following examples which are illustrative and not limitative of the present invention.

EXAMPLE 1

To a solution of 7.9 g. of 3-ethoxycarbonyl-8-(4-p-fluorophenyl-4-oxobutyl)-1-thia-4,8-diazaspiro[4.5]-decane in 80 ml. of benzene are added 4 g. of methyl isocyanate and 1 ml. of triethylamine, and the mixture is refluxed for 7 hours. After cooling, the reaction mixture is concentrated under reduced pressure. The resulting crystals are collected by filtration and recrystallized from 2-propanol to give 7 g. of 5,7-dioxo-6-methylimidazolido[1,5-c]thiazolidine-3-spiro-4'-[1'-(4-p-fluorophenyl-4-oxobutyl)piperidine] as white crystals melting at 128°–129°C. Its hydrochloride melts at 244°C with decomposition and its maleate melts at 182°–183°C.

EXAMPLE 2

A mixture of 5 g. of 3-ethoxycarbonyl-8-(4-p-fluorophenyl-4-oxobutyl)-1-thia-4,8-diazaspiro[4.5]-decane and 1.3 g. of methyl isothiocyanate in 50 ml. of pyridine is refluxed for 5.5 hours. After cooling, the pyridine is distilled off under reduced pressure and the residue is extracted with benzene. The benzene layer is washed twice with water and dried over anhydrous magnesium sulfate, and then the benzene is distilled off. The crystals obtained are washed with ethanol and recrystallized twice from ethanol to give 2.5 g. of 6-methyl-7-oxo-5-thioxoimidazolido[1,5-c]thiazolidine-3-spiro-4'-[1'-(4-p-fluorophenyl-4-oxobutyl)piperidine] as white crystals melting at 149°C.

EXAMPLE 3

To a solution of 10 g. of 3-ethoxycarbonyl-8-(4-p-fluorophenyl-4-oxobutyl)-1-thia-4,8-diazaspiro[4.5]-decane in 40 ml. of 70% glacial acetic acid is added 5 g. of potassium cyanate in small portions with stirring. The mixture is stirred at room temperature for about 30 minutes and then heated at 60°–75°C with stirring for 2.5 hours. After cooling, water is added to the reaction mixture and the reaction mixture is made alkaline with potassium carbonate. The resulting jelly-like substance is allowed to stand for some time to cause crystallization. The crystals are collected by filtration, washed with water and recrystallized from methanol to give 6 g. of 5,7-dioxoimidazolido[1,5-c]thiazolidine-3-spiro-4'-[1'-(4-p-fluorophenyl-4-oxobutyl)piperidine] as white crystals melting at 190°–191°C with decomposition. Its hydrochloride melts at 271°C with decomposition.

EXAMPLE 4

To a solution of 12.7 g. of 8-benzyl-3-ethoxycarbonyl-1-thia-4,8-diazaspiro[4.5]decane in 80 ml. of benzene are added 4 g. of methyl isocyanate and 1.5 ml. of triethylamine, and the mixture is refluxed for 8 hours. After cooling, the benzene is distilled off under reduced pressure. The residue is recrystallized twice from 2-propanol to give 9.5 g. of 5,7-dioxo-6-methylimidazolido[1,5-c]thiazolidine-3-spiro-4'-(1'-benzylpiperidine) as white crystals melting at 138°C.

EXAMPLE 5

A mixture of 9.6 g. of 8-benzyl-3-ethoxycarbonyl-1-thia-4,8-diazaspiro-[4.5]decane and 3 g. of methyl isothiocyanate in 60 ml. of pyridine is refluxed for 3 hours. After cooling, the pyridine is distilled off under reduced pressure and the residue is extracted with benzene. The benzene layer is washed twice with water and dried over anhydrous magnesium sulfate, and then the benzene is distilled off. The crystals obtained are washed with ethanol and recrystallized from ethanol to give 7 g. of 6-methyl-7-oxo-5-thioxoimidazolido[1,5-c]thiazolidine-3-spiro-4'-(1'-benzylpiperidine) as white crystals melting at 124°–125°C.

EXAMPLE 6

To a solution of 32 g. of 3,8-diethoxycarbonyl-1-thia-4,8-diazaspiro-[4.5]decane in 120 ml. of 70% glacial acetic acid is added 16 g. of potassium cyanate in small portions with stirring. The mixture is stirred at room temperature for about 30 minutes and then heated at 50°–60°C with stirring for 2 hours. Crystals begin to precipitate. The mixture is further heated at 50°–60°C with stirring for additional 2 hours. After cooling, water is added to the reaction mixture. The resulting crystals are collected by filtration, washed with water and recrystallized from methanol to give 25 g. of 5,7-dioxoimidazolido[1,5-c]thiazolidine-3-spiro-4'-(1'-ethoxycarbonylpiperidine) as white crystals melting at 242°–243°C.

EXAMPLE 7

A mixture of 10 g. of 5,7-dioxoimidazolido[1,5-c]thiazolidine-3-spiro-4'-(1'-ethoxycarbonylpiperidine) and 100 ml. of 20% hydrogen bromide solution in acetic acid is warmed on a water bath for 3 hours. After cooling, the solvent is distilled off under reduced pressure. The crystaline precipitate is collected by filtration, washed with methanol and recrystallized from 80% ethanol to give 5 g. of 5,7-dioxoimidazolido[1,5-c]thiazolidine-3-spiro-4'-piperidine hydrobromide as white crystals melting at 285°C with decomposition. Its hydrochloride melts at 289°C with decomposition.

EXAMPLE 8

A mixture of 10 g. of 6-methyl-5,7-dioxoimidazolido[1,5-c]thiazolidine-3-spiro-4'-(1'-ethoxycarbonylpiperidine) and 100 ml. of 20% hydrogen bromide solution in acetic acid is warmed on a water bath for 3 hours. After cooling, the solvent is distilled off under reduced pressure. The crystals are collected by filtration, washed with ethanol and recrystallized from methanol to give 5.5 g. of 6-methyl-5,7-dioxoimidazolido[1,5-c]thiazolidine-3-spiro-4-piperidine hydrobromide as white crystals melting at 265°C with decomposition.

EXAMPLE 9

To a mixture of 10 g. of potassium hydroxide, 300 ml. of methanol and 20 ml. of water is added 15 g. of 6-benzyl-5,7-dioxoimidazolido[1,5-c]thiazolidine-3-spiro-4'-(1'-ethoxycarbonylpiperidine) and the whole mixture is refluxed for 15 hours. After cooling, the solvent is distilled off under reduced pressure and water is added to the residue. The resulting oil is taken up with chloroform. The extract is washed with water, dried over anhydrous magnesium sulfate and then the chloroform is distilled off. The residue is dissolved in ethanol and to the solution is added ethanolic hydrochloric acid. The crystaline precipitate is collected by filtration and recrystallized from ethanol to give 8 g. of 6-benzyl-5,7-dioxoimidazolido[1,5-c]thiazolidine-3-spiro-4'-piperidine hydrochloride as white crystals melting at 212°–213°C.

EXAMPLE 10

To a mixture of 30 ml. of dimethylformamide and 30 ml. of toluene are added 5 g. of 6-methyl-5,7-dioxoimidazolido[1,5-c]thiazolidine-3-spiro-4'-piperidine, 4.5 g. of 4-p-fluorophenyl-4-oxobutyl chloride and 5 g. of sodium carbonate. The whole mixture is refluxed with stirring for 12 hours. After cooling, an insoluble matter is filtered off and the filtrate is concentrated under reduced pressure. The crystals obtained are recrystallized from 2-propanol to give 5 g. of 6-methyl-5,7-dioxoimidazolido[1,5-c]thiazolidine-3-spiro-4'-[1'-(4-p-fluorophenyl-4-oxobutyl)piperidine] as white crystals melting 128°–129°C. Its hydrochloride melts at 244°C with decomposition and its maleate melts at 182°–183°C.

EXAMPLE 11

To a mixture of 50 ml of dimethylformamide and 50 ml. of toluene are added 11 g. of 5,7-dioxo-6-phenylimidazolido[1,5-c]thiazolidine-3-spiro-4'-piperidine hydrobromide, 5 g. of 4-p-fluorophenyl-4,4-ethylenedioxybutyl chloride, a catalytic amount (about 0.3 g.) of potassium iodide and 15 g. of sodium carbonate. The whole mixture is refluxed with stirring for 10 hours. After cooling, an insoluble matter is filtered off and the filtrate is concentrated under reduced pressure to give 8 g. of crude 5,7-dioxo-6-phenylimidazolido-[1,5-c]thiazolidine-3-spiro-4'-[1'-(4-p-fluorophenyl-4,4-ethylenedioxybutyl)piperidine] as brown jelly. The crude product is added to a mixture of 200 ml. of ethanol and 50 ml. of 10% hydrochloric acid, and the whole mixture is warmed for 30 minutes. After cooling, the solvent is distilled off. The crystals obtained are recrystallized from a mixture of ethanol and water to give 5.5 g. of 5,7-dioxo-6 -phenylimidazolido[1,5-c]thiazolidine-3-spiro-4'-[1'-(4-p-fluorophenyl-4-oxobutyl)-piperidine] hydrochloride as white crystals melting at 256°C with decomposition.

EXAMPLE 12

To a solution of 2.8 g. of potassium hydroxide in 200 ml. of ethanol and 10 ml. of water is added 15.6 g. of 5,7-dioxoimidazolido[1,5-c]thiazolidine-3-spiro-4'-[1'-(4-p-fluorophenyl-4-oxobutyl)piperidine] and the mixture is refluxed for 2.5 hours. After cooling, the solvent is distilled off. The resulting potassium salt of the starting material is dissolved in 80 ml. of dimethylformamide, and then 9 g. of methyl iodide is added to the solution with stirring. After heating the mixture at 50°–60°C for 2 hours, the solvent is distilled off and the residue is extracted with ethyl acetate. The extract is washed with water, and dried, and the solvent is distilled off. The crystals obtained are recrystallized twice from 2-propanol to give 13 g. of 5,7 -dioxo-6-methylimidazolido[1,5-c]thiazolidine-3-spiro-4'-[1'-(4-p-fluorophenyl-4-oxobutyl)piperidine] as white crystals melting at 128°–129°C. Its hydrochloride melts at 244°C with decomposition and its maleate melts at 182°–183°C.

EXAMPLE 13

To a mixture of 2 g. of 50% sodium hydride and 50 ml. of dimethylformamide is added 9 g. of 5,7-dioxoimidazolido[1,5-c]thiazolidine-3-spiro-4'-[1'-(4-p-fluorophenyl-4-oxobutyl)piperidine]. After stirring at room temperature for 1 hour, 5.5 g. of phenethyl bromide is added to the reaction mixture and the whole mixture is stirred at 60°–70°C for 2.5 hours. The reaction mixture is poured into water. An oil which separates out is extracted with ethyl acetate. The extract is washed with water, dried and then the solvent is distilled off. The jelly-like residue is converted into the maleate in a conventional manner and the maleate is recrystallized twice from ethanol to give 6.9 g. of 5,7-dioxo-6-phenethylimidazolido[1,5-c]-thiazolidine-3-spiro-4'-[1'-(4-p-fluorophenyl-4-oxobutyl)piperidine] maleate as white crystals melting at 167°–168°C.

EXAMPLE 14 TO 63

Using the procedures set forth in the above examples, but substituting equivalent amount of the appropriate starting materials, the following compounds are also produced:

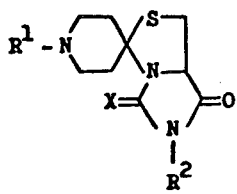

While the invention has been described in detail and with reference to specific embodiments thereof, it will be apparent to one skilled in the art that various changes and modifications can be made therein without departing from the spirit and scope thereof.

What is claimed is:

1. A compound of the formula:

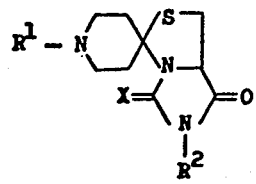

wherein $R^1$ represents a member selected from the group consisting of a hydrogen atom, an alkyl group of from 1 to 4 carbon atoms, a benzyl group, a p-chlorobenzyl group, a 4,5-dimethoxybenzyl group, a 4,5,6-trimethoxybenzyl group, a phenethyl group, an acetyl group, a benzoyl group, a trimethoxybenzoyl group, a methoxycarbonyl group, an ethoxycarbonyl group, a 4,4-bis(p-fluorophenyl)butyl group and a group of the formula

| Example | $R^1$ | $R^2$ | X | M.p. (°C) of base and/or salt |
|---|---|---|---|---|
| 14 | H | phenyl | O | HBr 291–292 |
| 15 | H | p-chlorophenyl | O | HBr 286 (dec) |
| 16 | H | o-tolyl | O | HBr 279 (dec) |
| 17 | H | p-nitrophenyl | O | HBr 268 (dec) |
| 18 | H | cyclohexyl | O | HBr 249–250 (dec) |
| 19 | methyl | H | O | base 212–213 |
| 20 | methyl | methyl | O | base 124–125 |
| 21 | butyl | methyl | O | HCl 254 (dec) |
| 22 | benzyl | H | O | base 195, HCl 287 (dec) |
| 23 | benzyl | phenyl | O | base 168–170 |
| 24 | benzyl | allyl | O | base 118–119 |
| 25 | benzyl | propargyl | O | maleate 111–113 |
| 26 | benzyl | phenethyl | O | HCl 239 (dec) |
| 27 | benzyl | cinnamyl | O | HCl 269 (dec) |
| 28 | p-chlorobenzyl | H | O | base 198 |
| 29 | p-chlorobenzyl | p-chlorobenzyl | O | base 135 |
| 30 | 3,4-dimethoxybenzyl | H | O | HCl 272 (dec) |
| 31 | 3,4-dimethoxybenzyl | methyl | O | HCl 254 (dec) |
| 32 | 3,4,5-trimethoxybenzyl | methyl | O | base 118 |
| 33 | phenethyl | H | O | base 176–177 |
| 34 | phenethyl | methyl | O | base 145–146 |
| 35 | acetyl | phenyl | O | base 187–188 |
| 36 | benzoyl | H | O | base 246 (dec) |
| 37 | benzoyl | methyl | O | base 161 |
| 38 | 3,4,5-trimethoxybenzoyl | methyl | O | base 180–181 |
| 39 | ethoxycarbonyl | α-naphthyl | O | base 226 |
| 40 | ethoxycarbonyl | p-clorophenyl | O | base 152–153 |
| 41 | ethoxycarbonyl | cyclohexyl | O | base 121 |
| 42 | ethoxycarbonyl | benzyl | S | base 135–136 |
| 43 | ethoxycarbonyl | p-nitrophenyl | O | base 205 |
| 44 | ethoxycarbonyl | p-tolyl | O | base 151–152 |
| 45 | ethoxycarbonyl | benzyl | O | base 142–143 |
| 46 | phenacyl | methyl | O | base 179–180 |
| 47 | p-methoxyphenacyl | methyl | O | base 181–182 |
| 48 | 3-p-fluorophenyl-3-oxopropyl | methyl | O | base 157–158 |
| 49 | 4-p-fluorophenyl-4-oxobutyl | ethyl | O | base 104 |
| 50 | 4-p-fluorophenyl-4-oxobutyl | butyl | O | HCl 170–173 |
| 51 | 4-p-fluorophenyl-4-oxobutyl | cyclohexyl | O | HCl 235–236 (dec) |
| 52 | 4-p-fluorophenyl-4-oxobutyl | o-chlorophenyl | O | base 140–141 |
| 53 | 4-p-fluorophenyl-4-oxobutyl | p-chlorophenyl | O | base 104–106 |
| 54 | 4-p-fluorophenyl-4-oxobutyl | 2,5-dichlorophenyl | O | base 121–123 |
| 55 | 4-p-fluorophenyl-4-oxobutyl | o-tolyl | O | HCl 215 |
| 56 | 4-p-fluorophenyl-4-oxobutyl | o-nitrophenyl | O | base 172 |
| 57 | 4-p-fluorophenyl-4-oxobutyl | p-nitrophenyl | O | base 138 |
| 58 | 4-p-fluorophenyl-4-oxobutyl | α-naphthyl | O | HCl 253 (dec) |
| 59 | 4-p-fluorophenyl-4-oxobutyl | benzyl | O | oxalate 198 (dec) |
| 60 | 4-p-fluorophenyl-4-oxobutyl | allyl | O | HCl 185–186 |
| 61 | 4-p-fluorophenyl-4-oxobutyl | propargyl | O | HCl 242–243 (dec) |
| 62 | 4-p-fluorophenyl-4-oxobutyl | cinnamyl | O | HCl 211–212 |
| 63 | 4,4-bis(p-fluorophenyl)butyl | methyl | O | maleate 186 | dec: decomposition

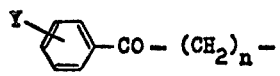

(in which Y represents a member selected from the group consisting of H, F and $CH_3O$, and $n$ represents an integer of 1, 2 or 3); $R^2$ represents a member selected from the group consisting of a hydrogen atom, an alkyl group of from 1 to 4 carbon atoms, an allyl group, a propargyl group, a cyclohexyl group, a phenyl group, a chlorophenyl group, a dichlorophenyl group, a tolyl group, a nitrophenyl group, a naphthyl group, a benzyl group, a phenethyl group and a cinnamyl group; and X represents a member selected from the group consisting of an oxygen atom and a sulphur atom, and pharmaceutically acceptable acid addition salts thereof.

2. A compound of the formula:

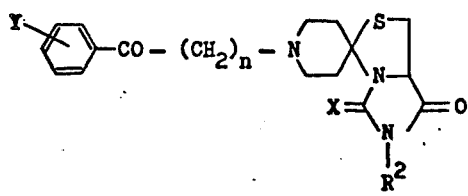

wherein Y represents a member selected from the group consisting of a hydrogen atom, fluorine atom and a methoxy group; $n$ represents an integer of 1, 2 or 3; $R^2$ represents a member selected from the group consisting of a hydrogen atom, an alkyl group of from 1 to 4 carbon atoms, an allyl group, a propargyl group, a cyclohexyl group, a phenyl group, a chlorophenyl group, a dichlorophenyl group, a tolyl group, a nitrophenyl group, a naphthyl group, a benzyl group, a phenethyl group and a cinnamyl group; and X represents a member selected from the group consisting of an oxygen atom and a sulphur atom, and pharmaceutically acceptable acid addition salts thereof.

3. A compound of the claim 1:
5,7-dioxo-6-methylimidazolido[1,5-c]thiazolidine-3-spiro-4'-[1'-(4-p-fluorophenyl-4-oxobutyl)piperidine].

4. A compound of the claim 1:
5,7-dioxo-6-ethylimidazolido[1,5-c]thiazolidine-3-spiro-4'-[1'-(4-p-fluorophenyl-4-oxobutyl)piperidine].

5. A compound of the claim 1:
5,7-dioxo-6-butylimidazolido[1,5-c]thiazolidine-3-spiro-4'-[1'-(4-p-fluorophenyl-4-oxobutyl)piperidine].

6. A compound of the claim 1:
5,7-dioxoimidazolido[1,5-c]thiazolidine-3-spiro-4'-[1'-(4-p-fluorophenyl-4-oxobutyl)piperidine].

7. A compound of the claim 1:
5,7-dioxo-6-o-tolylimidazolido[1,5-c]thiazolidine-3-spiro-4'-[1'-(4-p-fluorophenyl-4-oxobutyl)piperidine].

8. A compound of the claim 1:
5,7-dioxo-6-p-nitrophenylimidazolido[1,5-c]thiazolidine-3-spiro-4'-[1'-(4-p-fluorophenyl-4-oxobutyl)-piperidine].

9. A compound of the claim 1:
5,7-dioxo-6-cyclohexylimidazolido[1,5-c]thiazolidine-3-spiro-4'-[1'-(4-p-fluorophenyl-4-oxobutyl)-piperidine].

10. A compound of the claim 1:
5,7-dioxo-6-α-naphthylimidazolido[1,5-c]thiazolidine-3-spiro-4'-[1'-(4-p-fluorophenyl-4-oxobutyl)-piperidine].

* * * * *